US006511959B1

(12) United States Patent
Logothetou-Rella

(10) Patent No.: US 6,511,959 B1
(45) Date of Patent: Jan. 28, 2003

(54) USE OF CALCIUM-ACTIVATED NEUTRAL PROTEASE (CANP) INHIBITORS IN PHARMACEUTICAL PREPARATIONS

(75) Inventor: Helen Logothetou-Rella, Athens (GR)

(73) Assignee: Norsk Hydro AS, Oslo (NO)

( * ) Notice: Subject to any disclaimer, the term of this patent is extended or adjusted under 35 U.S.C. 154(b) by 0 days.

(21) Appl. No.: 09/610,995

(22) Filed: Jul. 6, 2000

Related U.S. Application Data

(63) Continuation of application No. 08/394,519, filed on Feb. 27, 1995, now abandoned, which is a continuation-in-part of application No. 07/978,682, filed as application No. PCT/EP92/01223 on Jun. 2, 1992, now abandoned.

(30) Foreign Application Priority Data

Jun. 3, 1991 (GR) ......... 910100238

(51) Int. Cl.⁷ ......... A61K 38/00; C07K 14/00; C07K 5/08
(52) U.S. Cl. ......... 514/2; 514/18; 530/324; 530/331; 530/350; 435/219; 560/174
(58) Field of Search ......... 530/324, 331, 530/350; 514/2, 18; 435/219; 560/174

(56) References Cited

U.S. PATENT DOCUMENTS

| | | | |
|---|---|---|---|
| 4,891,356 A | 1/1990 | Szabo | 514/2 |
| 5,081,284 A | 1/1992 | Higuchi et al. | 560/159 |
| 5,189,144 A | 2/1993 | Asada et al. | 530/324 |
| 5,340,922 A | 8/1994 | Nixon et al. | 530/350 |
| 5,444,042 A | 8/1995 | Bartus et al. | 514/2 |
| 5,510,531 A | 4/1996 | Higuchi et al. | 564/159 |
| 6,294,518 B1 * | 9/2001 | Potter et al. | 514/12 |

OTHER PUBLICATIONS

Oxford Textbook of Oncology, vol. 1. Peckham et al., Editors. Oxford University Press. pp. 566 and 571. 1995.
Melloni et al., Regulation of the $Ca^{2+}$–Dependent Neutral Proteinases from Rabbit Liver by an Endogenous Inhibitor, Arc. Biochem Biophy. 232 (2) 1984 pp. 513–519.
Shea et al., Multiple Proteases Regulate Neurite Outgrowth in NB2a/dl Neuroblastoma Cells, J. Neurochemistry 56 (3) 1991 pp. 842–851.
AIDS Drugs Beyond Access, "The Economist" Jan. 8, 1994 79.
Nishiura et al., The role of Intracellular Proteases in Brain Tumor, Neurol. Med. Chin 1979 19(1) 1–8.
Logothetou–Rella, Histol. Histopath (1993) 8:739–750.
Logothetou–Rella, Histol. Histopath (1993) 8:407–423.
Logothetou–Rella, Histol. Histopath (1994) 9:469–484.
Logothetou–Rella, Histol. Histopath (1994) 9 (pages unnumbered in press).
Logothetou–Rella, Histol. Histopath (1994) 9:485–493.
Logothetou–Rella, Histol. Histopath (1994) 9:243–249.
Logothetou–Rella, European Urology, 1992; 21 147–150.
Logothetou–Rella, The Inhibitor of Calcium Activated Neural Proteinase is an Anti–Meiotic Agent, The Spermicidal and Anti–Viral Action.

* cited by examiner

Primary Examiner—Karen Cochrane Carlson
Assistant Examiner—Chih-Min Kam
(74) Attorney, Agent, or Firm—Wenderoth, Lind & Ponack, L.L.P.

(57) ABSTRACT

The invention provides to the use of inhibitors of calcium-activated neutral proteases (CANPs) and their pharmaceutically acceptable addition salts or their active subunits in the field of tumor therapy, especially cancer therapy. The inhibitors can especially be used against protease-bound bound glycosaminoglycan substrate-dependent tumors and meiotic cell division. The inhibitors include heat-stable, tetrameric proteins of approximately 240 kD possessing active subunits, and tripeptides exhibiting inhibitory activity. The pharmaceutical compositions may be prepared in a manner known per se, with carriers or additives commonly used in the pharmaceutical industry.

19 Claims, 3 Drawing Sheets

The effect of protease inhibitors on cell survival of human NHIK 3025 cervix carcinoma cells *in vitro*.

The effect of CANP inhibitor on cell survival of human NHIK 3025 cervix carcinoma cells *in vitro*. The CANP inhibitor was chromatographically purified.

The effect of calpain inhibitors I and II on growth of Walker rat tumors

USE OF CALCIUM-ACTIVATED NEUTRAL PROTEASE (CANP) INHIBITORS IN PHARMACEUTICAL PREPARATIONS

This application is a continuation of application Ser. No. 08/394,519 filed Feb. 27, 1995, now abandoned, which is a continuation-in-part of application Ser. No. 07/978,682 filed Mar. 25, 1993, now abandoned, which is a 371 of international application No. PCT/EP92/01223 filed Jun. 2, 1992.

FIELD OF THE INVENTION

The present invention relates to the pharmaceutical use of specific inhibitors of calcium-activated neutral proteases (CANPs). More specifically, the inhibitors may be especially used for the treatment of tumors, especially cancer. The inhibitors may be proteinaceous of character, subunits of said inhibitor proteins, or shorter peptides. The invention further relates to the manufacture of pharmaceutical preparations for the treatment of the above mentioned diseases.

BACKGROUND OF THE INVENTION

Calcium-activated neutral proteases (CANPs), also known as calpain I and II, are cysteine proteases found in the cells of higher animals. They have been presumed to participate in various cellular functions mediated by calcium, but their precise function is not yet understood. Calpain I requires low concentrations of calcium to be functional (also refered to as $\mu$-CANP) while calpain II requires millimolar concentrations of calcium (refered to as m-CANP). CANPs hydrolyse proteins of limited classes in vitro, including epidermal growth factor receptor, platelet derived growth factor receptor and protein kinase C. They appear to be involved in regulating the turnover and degradation of muscle myofibrillar proteins and neuronal cytoskeletal elements Murachi T., 1983, *Trends Biochem. Sci.*, 8:167), suggesting that CANPs are involved in essential cellular functions associated with meiosis (as supported in WO 92/21373 and Logothetou-Rella H., 1994, *Histol. Histopath.*, 9:747).

Calcium-activated neutral protease inhibitors have been used to indirectly document CANP involvement in a variety of different diseases. CANP inhibitors have been suggested for use in the treatment of myocardial infarction, ischemia and potential stroke using inhibition of platelet CANP (Puri and Colman, 1993, *Blood Coagul. & Fibrin*, 4:465). The degradation process of the ischemic heart is contributed to CANP (Toyo-oka et al., 1991, *Japan Circulat. J.*, 55:1124). CANP is found in the brain of patients suffering from Alzheimer's disease (Saito et al., 1993, *Proc. Natl. Acad. Sci.*, 90:2628), muscular dystrophy (Hollenberg-Sher et al., 1981, *Proc. Natl. Acad. Sci.*, 78:7742), and may play a role in the inflammatory process (Sasaki et al., 1991, *Acta Biologica Hungarica*, 42:231 and Logothetou-Rella H., 1994, *Histol Histopath.*, 9:469).

One of the most lethal properties of malignant cells is their ability to infiltrate normal tissues and to metastasize to distant areas. The normal connective tissues consist of cells embedded in an extracellular matrix containing glycoproteins, collagen, elastin, and proteoglycans. There have been suggestions that tumor-associated histolytic enzymes may aid in the invasive process by removal of the matrix protein (Hart, I. et al., 1980, *JNCI* 64:891). Several studies have concentrated on this aspect of tumor cell biology, and increased protease production has been observed with many transformed cells (Jones, P. A. and Declerk Y. A., 1980, *Cancer Res.*, 40:3222).

It has been reported that malignant cells in culture from human invasive urothelial carcinoma form tumor nodules and glycosaminoglycan membraneous sacs (GSG) with membrane extensions intracellularly as well as extracellularly (Logothetou-Rella H. et al., 1988, *Europ. Urol.* 14:61, ibid, 14:65). The same observations were made in human embryonic cell cultures Logothetou-Rella H. et al., 1989, *Histol. Histopath.*, 4:367), while they were not found in human normal urothelial cells in culture (Logothetou-Rella H. et al., 1988, *Europ. Urol.*, 15:259). The participation of GSG has also been reported in capillary formation which is enhanced in tumors in vivo (Logothetou-Rella H. et al., 1990, *Histol Histopath.*, 5:55).

The characteristic extracellular matrix (GSG) of malignant and embryonic cells is PAS and PAS-diastase positive, identified by Papanicolaou stain having a light green color (EA color) and smooth to fibrillar translucent texture. GSG in malignant cells is distributed and accumulated in intracellular and extracellular membraneous sacs. The membraneous GSG sacs give rise to membrane extensions which form channels through which the green GSG is passed from the inside to the outside of the cell. This structure also enhances tumor nodule formation and invades other cells in vitro. It was further documented that this extracellular matrix (ECM) consisted of GSG bound protease resulting from cell to cell invasion (Logothetou-Rella, H., Greek patent 910100238, Mar. 6, 1991, WO92/21373, Logothetou-Rella, H. et al., 1992, *Eur. Urol.* 21:146, Logothetou-Rella, H., 1994, *Histol Histopath.*, 9:243).

Nuclear vlima (NV, nuclear bullets) defines a parasitic spermatozoo-like cell produced by assymetrical, unequal cell division invading other cells (as supported by WO 92/21373 and Logothetou-Rella, H., 1993, *Histol. Histopath.*, 8:407). NVs have been identified in malignant, embryonic, virally infected cells (Logothetou-Rella, H., 1994, *Histol. Histopath.*, in press) and PHA-activated lymphocytes (Logothetou-Rella, H., 1994, *Histol. Histopath.*, 9:469). Furthermore, NVs carry aneuploid sets of chromosomes, invade other host cells forming hybrids with a process similar to fertilization or viral cell infection and are sensitive to CANP inhibitors (Logothetou-Rella, H., Greek patent 910100238, Mar. 6, 1991, WO92/21373, and Logothetou-Rella, H., 1994, *Histol. Histopath.*, 9:469, ibid 9:485, ibid 9:747).

OBJECT OF THE INVENTION

Surprisingly, a new mechanism of cell to cell invasion subsequent to meiotic cell division and substrate (GSG bound CANP) formation, common in formation of tumors was discovered. Moreover, it was found that administering specific inhibitors of CANPs, or active subunits, thereof providing an effective concentration of said inhibitors in the human or animal body, would inhibit the aforementioned processes.

DETAILED DESCRIPTION OF THE INVENTION

Figure 1:
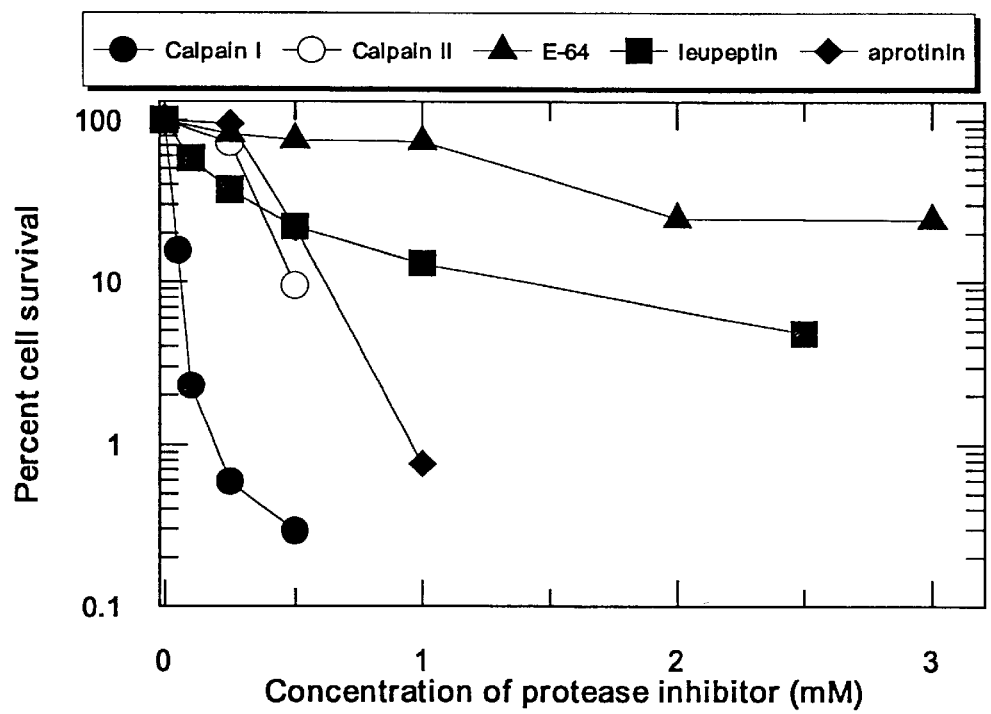
FIG. 1 is a graph showing the effect of protease inhibitors on cell survival of human HNIK 3025 cervix carcinoma cells in vitro.

The endogenous, native, inhibitor of CANPs used in the invention is preferably a tetrameric protein having a molecular weight of approximately 240,000 Dalton. The protein is heat stable at neutral pH and is destroyed upon digestion with trypsin. Furthermore, the native inhibitor of CANPs can be dissociated into subunits of approximately 60,000 Dalton based upon SDS-polyacrylamide gel electrophoresis (as described by Melloni, E. et al., 1984, *Arch. Biochem. Biophys.* 232:513). All pharmaceutical acceptable salts, derivatives, analogues or active subunits of different molecular weights thereof can also be used as specific inhibitors of CANPs.

The inhibitor may be endogenous native inhibitor of CANP isolated from a biological source, like erythrocytes, brain, cardiac muscle, lung, spleen, liver, skeletal muscle, kidney, testis or the like, and optionally purified, but especially from rabbit skeletal muscle or liver. A preferred inhibitor isolated from rabbit skeletal muscle is commercially available from Sigma Chemical Company, St. Louis, Mo., USA and is referred to as P 0787 Protease Inhibitor: Inhibitor of calcium-activated neutral protease (Sigma Chemical Co. catalog, 1990, page 889, Melloni, E. et al., 1984, *Arch. Biochem. Biophys.* 232:513). The inhibitors or active fragments thereof, like subunits, derivatives, analogues of molecular weight 60,000 or lower may also be produced synthetically, especially by bio- or genetechnological methods, e.g., by expression in *Escherichia coli*.

It is believed that the MWs of the active subunits of the specific inhibitor depend on the substrates (e.g. casein, denatured globin etc.) used. Therefore, the MW of the active part of the inhibitor may be lower than 60,000.

Calpastatin and many other specific inhibitors of CANP, of different MWs (which depend on the substrates used) have been reported in the literature (Tanako and Murachi, 1992, *J. Biochem.*, 92:2021, and Hatanaka et al., 1983, *Biomed. Res.*, 4:381, and Emori et al., 1987, *Biochem.*, 84:3590, and Kawasaki et al., 1989, *J. Biochem.*, 106:274, and Takano et al., 1991, *Bioch Med. and Metab. Biol.*, 45:41). The tripeptide compounds Calpain inhibitor I (N-Acetyl-Leu-Leu-Norleucinal) and Calpain inhibitor II (N-Acetyl-Leu-Leu-Methioninal), are known to inhibit the low calcium requiring (calpain I) or high calcium requiring (calpain I) forms of CANP, respectively (Kajiwara, Y. et al., 1987, *Biochem. Int.*, 15:935 and Murachi, I. 1983, *Trends Biochem. Sci.*, 8:167). These inhibitors of CANP are commercially available from Boehringer Mannheim GmbH, Biochemica, D-68298 Mannheim, Germany referring to product number 1086 090 for calpain inhibitor I and product number 1086 103 for calpain inhibitor II (Boehringer Mannheim catalog, 1994, page 188).

In the present invention, the pharmaceutical preparation may be in the form of a solution, powder, injection, tablet, capsule, pellets, in a fast or sustained release form, each containing a suitable amount of a specific native or synthetic and eventually purified inhibitor or its pharmaceutically acceptable addition salts, active subunits, fragments, derivatives, analogues or related compounds together with well-known suitable excipients.

The inhibitors may preferably be administered to humans and warm blooded animals intramuscularly, subcutaneously, intraperitoneally, or intravenously in an amount which depends upon the kind and severity of the disease, the inhibitory effect of the inhibitor, the route of administration, the species to be treated, the weight and the general condition of the patient, and in most cases has to be finally decided by the responsible physician. In general the dose is between about 1 mg/kg per day and 25 mg/kg per day. However, if needed, higher doses, e.g., up to 100 mg/kg per day, may be administered.

The surprising effect of the inhibitors of CANPs has been confirmed and verified by the following examples. Where appropriate comparison between specific inhibitors of CANPs and other protease inhibitors, such as aprotinin, leupeptin and E64, are given to demonstrate the marked effect of inhibitors of CANP towards cancer cell growth. In studying the role of CANPs in the above processes, several exogenous inhibitors of CANP have been utilized. Leupeptin, a peptide of the structure N-acetyl-L-leucyl-L-leucyl-L-arginal, and E64, an epoxy compound of the formula L-trans-3-carboxy-oxiran-2-carbonyl-L-leucylagmatine, are both specific inhibitors of thiol proteases.

EXAMPLE 1

The use of the native inhibitor of CANP for inhibiting growth and viability of malignant cells in vitro.

Cell Cultures

Monolayer cell cultures were established from human solid tumor tissue specimens by enzymatic digestion. Malignant lung cell lines from metastatic lung carcinoma, M-cells, P-cells and B-cells, have recently been characterized (Logothetou-Rella, H. et al., 1992, *Exp. Clin. Cancer Res.*, 11(4):285). Malignant urothelial cell cultures were established from tissue specimens from patients with invasive transitional cell carcinoma. The five established urothelial malignant cell lines were designated as Pa-cells, R-cells, S-cells, Br-cells and IG-cells. Only the patient from which Pa-cells were derived had received bladder intravesical infusions of anticancer drugs. A melanoma cell culture (Ha-cells) originated from a tissue specimen from the lymph nodes of the right arm representing metastases from a primary rectal melanoma in a male patient (Logothetou-Rella, H., 1993, *Histol. Histopath.*, 8:407).

Malignant bone marrow cells originating from bone marrow aspirates from five patients with chronic myeloid leukemia were obtained. Walker tumor rat cells were isolated from transplanted tumor tissue in Wistar rats. Normal human liver cells (L-cells) were isolated from a liver tissue specimen from a male patient who underwent surgery for the removal of his gall bladder.

Normal fallopian tube cells (F-cells) were isolated from a tissue specimen from a female patient who underwent a total hysterectomy. Normal bladder cells (N-cells) have been characterized previously (Logothetou-Rella, H. et al., 1988, *Europ. Urol.*, 15:259). White blood cells from five healthy volunteers were also used as control cells.

Amniotic embryonic cells from five pregnant women which were cultivated for prenatal diagnosis were also used in this study. All cell cultures were grown in complete medium RPMI-1640 supplemented with 10% fetal bovine serum, glutamine and antibiotics, and incubated at 37° C. in a humidified $CO_2$-incubator.

Cytogenetic Analysis

Chromosomal analysis of M-cells, P-cells and B-cells have recently been reported (WO 92/21373, Logothetou-Rella, H. et al., 1992, *J. Exper. Clin. Cancer Res.*, 11(4):285). Urothelial malignant Pa-cells consisted of malignant cell clones only, with polyploidy up to 147 chromosomes and complex structural abnormalities. Approximately 20% of the S-cell population consisted of malignant cell clones with regular tetraploidy while 80% were normal cell clones. Br-cells consisted of normal and malignant cell clones but detailed chromosomal analysis was unsuccessful. Melanoma Ha-cells displayed double minutes. Liver L-cells, fallopian tube F-cells, and amniotic embryonic cells were cytogenetically normal (Logothetou-Rella, H., 1993, *Histol. Histopath.*, 8:407).

Two techniques were used to determine the inhibitors cytotoxicity on tumor and normal cells.
a) Cytological Changes of Cell Cultures in Continuous Presence of the Inhibitors The following samples were made up in RPMI-1640 complete medium:

1. 1 U/ml CANP inhibitor
2. 2 mg/ml trypsin-chymotrypsin inhibitor
3. 1 mg/ml aprotinin
4. 1 mg/ml leupeptin
5. 1 mg/ml E64
6. all five inhibitors at the above mentioned concentrations
7. RPMI-1640 medium with no inhibitor addition to serve as a control medium.

Ten glass Petri dishes (5 cm diameter) were seeded each with $1 \times 10^6$ M-cells and another ten dishes were seeded each with $1 \times 10^6$ P-cells. Duplicate cell cultures received each type of complete medium containing the inhibitors and control cultures received only complete medium. The cell cultures were incubated at 37° C. in a humidified $CO_2$-incubator for 120 hours. The culture medium was changed with fresh medium containing the same inhibitors at 24 and 72 hours after start of the experiment. Half of the cell cultures were fixed in 50% ethanol 72 hours and the other half 120 hours after initiation of the experiment. All cell cultures were stained according to the Papanicolaou method.

Trypsin-chymotrypsin inhibitor, aprotinin, leupeptin and E64 did not affect the growth or cytology of M- and P-cells as compared to control cell cultures.

Post-confluent, monolayer cell cultures of malignant M-cells, P-cells and normal L-cells (20 days continuous cultivation) that had produced abundant extracellular matrix, received fresh complete medium RPMI-1640 supplemented with 1 U/ml of CANP inhibitor. Cells were incubated at 37° C. for 3 days, then fixed in 50% ethanol and stained according to the Papanicolaou method.

The inhibitor of CANPs caused great exfoliation of cells and extracellular matrix (ECM) in the culture medium after 72 hours of continuous presence in cultures. All exfoliated cells were no longer viable (according to trypan blue staining), and consisted of hyperchromatic, pyknotic nuclei, little cytoplasm and nuclei with tails. Some attached fibroblast-like cells (a few countable per microscopic field) were present on the culture dish surface and remained alive and cytologically normal. All other cell culture dishes, except those receiving CANP inhibitor (medium 1 and 6), and the control dishes were full of cells and nuclear vlima ("NV"; "vlima"=bullet) uncountable per microscope field, without cell exfoliation, with macroscopically apparent green, fibrillar, translucent ECM and GSG sacs. The observations were persistent after 120 hours of continuous presence of the CANP inhibitor in cell cultures, except that the surviving fibroblast-like cells had grown in the presence of the CANP inhibitor.

Post-confluent M- and P-cell cultures, in the presence of the inhibitor of CANP, exhibited cells with vacuolated cytoplasm and degenerated vacuolated nuclei of different sizes with or without tails. The rounded up, detached, dead cells were attached to each other and to the culture dish surface by a network of hematoxylinophilic (blue) membranes visible microscopically. The ECM and GSG sacs had disappeared. Instead large masses of hematoxylinophilic granules were visibly present.
b) Liquid Medium Short-term Culture Method (Chang, S. Y. et al., 1989, *Eur. Urol.*, 16:51)

The cells were detached with trypsin-EDTA, resuspended in complete RPMI-1640 medium and cell counts were made using a hemocytometer. Viable counts were assessed using the 0.4% trypan blue exclusion method. The cells were then washed once with complete RPMI-1640 medium, centrifuged at 200×g for 8 minutes, resuspended in complete RPMI-1640 at 30,000–200,000 cells per 0.5 ml medium and inoculated into sterile polypropylene tubes as shown below:

| Test tube case no. | CANP inhibitor (U/ml) | CANP inhibitor (ml) | Cell suspension (ml) | FBS* (ml) | Complete RPMI-1640 (ml) |
|---|---|---|---|---|---|
| 1 | 1 | 0.1 | 0.5 | — | 0.4 |
| 2 | 2 | 0.2 | 0.5 | — | 0.3 |
| 3 | 3 | 0.3 | 0.5 | — | 0.2 |
| 4 | 4 | 0.4 | 0.5 | 0.05 | 0.05 |
| 5 | 5 | 0.5 | 0.45 | 0.05 | — |
| 6 | 6 | 0.6 | 0.35 | 0.05 | — |
| 7 | 0 | 0.0 | 0.5 | — | 0.5 |

*FBS = fetal bovine serum

Duplicate samples of cells were tested for each concentration of the inhibitor. All samples were incubated and shaken in a water bath at 37° C. for one hour. Then the cells were washed twice with complete RPMI-1640 by centrifugation at 200×g for 8 minutes. Each rinsed cell pellet was resuspended in 1 ml complete RPMI-1640 and gently pipetted to obtain a single cell suspension. The cells were then seeded into 24-well microtiter plates for a 4-day period of short term culture at 37° C. in a humidified $CO_2$-incubator. The cytotoxicity assessment was done using the dye exclusion method with 0.4% trypan blue. The degree of cytotoxicity was measured according to the following formula:

$$\text{Cytotoxicity (\%)} = \left(1 - \frac{\text{Number of viable cells in the experimental group}}{\text{Number of viable cells in the control group}}\right) \times 100$$

The inhibitor of CANP selectively killed all types of malignant cells tested, in a dose-dependent manner (Table 1), while allowed normal cells within the same or separate culture to grow and propagate (Table 2). The optimum concentration of 4–5 U/ml inhibitor killed all malignant clones, while lower concentrations killed a lower percentage of malignant cells. Higher concentrations did not alter the results. The inhibitor was not cytotoxic to normal cells including liver cells, fallopian cells and WBCs. Cytogenetic analysis of the surviving cells (in mixed cell lines), after the CANP inhibitor treatment, showed normal karyotype. The inhibitor of CANP was also cytotoxic to embryonic cells.

TABLE 1

Cytogenetic state of each cell type used in studies described in example 1

| Tissue origin | Designation | Malignant and normal clones | Malignant clone | Normal clone |
|---|---|---|---|---|
| Bladder transitional cell carcinoma | Pa-cells | | + | |
| | Br-cells | + | | |
| | S-cells | + | | |
| | IG-cells | | + | |
| Lung carcinoma | R-cells | + | | |
| | M-cells | + | | |
| | P-cells | + | | |
| | B-cells | + | | |

TABLE 1-continued

Cytogenetic state of each cell type used in studies described in example 1

| Tissue origin | Designation | Malignant and normal clones | Malignant clone | Normal clone |
|---|---|---|---|---|
| Melanoma | Ha-cells | | + | |
| Chronic myeloid leukemia | BM-cells | | + | |
| Walker rat tumor | W-cells | | + | |
| Normal liver | L-cells | | | + |
| Normal urothelium | N-cells | | | + |
| White blood cells | WBC | | | + |
| Human amniotic embryonic cells | | | | + |
| Human fallopian cells | F-cells | | | + |

TABLE 2

Sensitivity of cells to different concentrations of CANP inhibitor
Inhibitor cytotoxicity (%)

| Tested cells | CANP inhibitor concentration (U/ml) | | |
|---|---|---|---|
| | 1 | 4 | 5 |
| M-cells | 24 | 65 | 65 |
| P-cells | 45 | 82 | |
| B-cells | 86 | 87 | |
| Pa-cells | 24 | 99 | 100 |
| S-cells | | 34 | |
| Br-cells | | 55 | |
| R-cells | | 83 | |
| IG-cells | | 100 | |
| Ha-cells | 21 | | 100 |
| Walker tumor cells | | 100 | |
| Malignant bone marrow cells | | 88–100 | |
| N-cells | 0 | 0 | 0 |
| L-cells | 0 | 0 | 0 |
| WBCs | 0 | 0 | 0 |
| Embryonic cells | 45 | 95 | 100 |
| F-cells | 0 | 0 | 0 |

The cytotoxicity of the inhibitor in each specimen was obtained from the mean of duplicate samples.

EXAMPLE 2

Use of the native inhibitor of CANP on the viability of normal and malignant urothelial tissues Tumor (from 5 patients) and normal (from 5 persons) tissue pieces of human urothelium of 2 mm×2 mm×2 mm size were rinsed in complete RPMI-1640 medium, handled gently with fine forceps. One piece of each type of tissue was immersed in complete RPMI-1640 (control) and one piece in the CANP inhibitor solution (10 U/ml) in polypropylene tubes and incubated at 37° C. for one hour in a humidified, 5% $CO_2$ incubator. All tissue pieces were then rinsed carefully in complete medium and subsequently immersed in polypropylene tubes (1 piece/tube) containing 2 ml complete RPMI-1640, then incubated for 4 days at 37° C. The tissue pieces were then fixed in formaldehyde, embedded in paraffin and tissue sections were stained with eosin-hematoxylin. The exfoliated cells in the tubes with the malignant tissue pieces were allowed to settle in a conical polypropylene tube for 10 minutes, then smeared onto glass slides, fixed with cytospray, and stained with Papanicolaou.

The inhibitor of CANPs caused massive cell exfoliation of the malignant tissues. Histologic examination of the inhibitor-treated malignant tissues exhibited bionecrotic to necrotic areas and large tissue areas consisting of eosinophilic extracellular matrix denuded of cells. The exfoliated cells were dead, with degenerated nuclei, and spermatozoa-like morphology, separated from each other and lacking the green ECM. The very few malignant tissue exfoliated cells, in the absence of the inhibitor of CANPs, showed compact cell masses in green ECM with indiscrete cell boundaries.

Normal urothelial tissues were kept intact after treatment with the inhibitor.

EXAMPLE 3

The use of the native inhibitor of CANP against rat tumors in vivo

Two Walker tumors were excised 2 weeks following the subcutaneous implantation of tumor tissue in male Wistar rats. Tumor cell suspensions for injection were prepared as described previously (Fisher E. R. and Fisher B., 1959, 12:926). A group of male Wistar rats, weighing 100 gr each, were injected with $10 \times 10^6$ Walker tumor cells subcutaneously in the left foot pad. The rats were then divided into four groups, two control and two treated. Treatment was initiated when tumors had reached a measurable size of 50–100 $mm^3$. The first group of rats was injected i.p., each rat with 50 U/2.5 ml (645 mg/2.5 ml) inhibitor of CANPs, once a day, for a period of 5 days (0.5 U/kg or 6.45 gr/kg rat body weight).

The second group of rats was treated intraperitoneally, twice daily for 5 days with a dose of 0.25 U/kg (3.23 gr/kg) rat body weight. Control rats were injected each with 2.5 ml medium RPMI-1640 containing 25 mM HEPES buffer. All rats were sacrificed 4 days after the last treatment, for the injected legs of the control groups were covered with tumors progressing up to the shoulder blade making accurate control tumor measurements impossible. The tumor-containing legs, lymph nodes and liver from all rats were excised, fixed in formalin and embedded in paraffin for histological studies. Tumor volumes were measured every day after the first dose using calipers.

The inhibitor of CANPs caused 50% tumor regression in the first group of treated rats and 90% in the second group. All groups (treated and control) started at time 0 without any significant difference in tumor volumes.

The rats under treatment were healthy and did not show any allergic reaction or side-effects to the high dose of the inhibitor (which originated from rabbit skeletal muscle). Histological examination of livers of the treated rats did not show any cytotoxic effects caused by the inhibitor, as central venules were observed without necrosis or cellular damage. Histological examination of the testis of treated rats showed pronounced spermatogenetic arrest. No other organs were affected.

Within the first treated group, one rat developed a metastatic abdominal focus and another one a metastatic hepatic focus. The feeling of the abdominal focus disappeared 24 hours after the first dose. Histological examination showed necrosis of a large carcinomatous nodule with formation of abscess, necrosis of the overlaying epidermis and ulceration. The liver metastatic focus was necrotized, exhibiting necrotic material with nuclear debris in the center and remnants of carcinomatous tissue with mitosis in its periphery. The foot pad tumors of treated rats showed necrotic areas of variable size with formation of microabscesses. These results become more important when taking into account the aggressiveness of Walker tumor cells (rats usually die 20 days after transplantation). These results have now been published (Logothetou-Rella, H., 1994, *Histol. Histopath.*, 9:485).

EXAMPLE 4

The effect of CANP inhibitor on survival of mice bearing L1210 leukemia

In vitro continuous treatment of murine L1210 leukemia cells with 0.25 U/ml CANP inhibitor induced a significant and large cytotoxic effect. Therefore, $1 \times 10^6$ L1210 cells were implanted i.p. into female DBA/2 mice. Treatment with 2 U CANP inhibitor/mouse/day began one day subsequent to tumor cell implantation. Mice were then treated daily by an intraperitoneal injection of CANP inhibitor until the time of death. The median life span (MLS) of placebo-treated mice was calculated to be 11.58±0.34 days, while that of CANP inhibitor-treated animals was 13.58±0.51 days (p=0.0036). This slight, although significant, increase in MLS is consistent with the in vitro sensitivity of L1210 cells to the inhibitor of CANP.

EXAMPLE 5

The effect of other CANP inhibitors on malignant cell survival

Human cells of the established line NHEK 3025, originating from a cervical carcinoma in situ (Nordbye, K. and Oftebro, R., 1969, *Exp. Cell Res.,* 58:458 and Oftebro, R. and Nordbye, K., 1969, *Exp. Cell Res.,* 58:459) were cultivated in medium Eagles minimum essential medium (MEM) supplemented with 10% fetal bovine serum and antibiotics. Cells were routinely grown as monolayers in tissue culture flasks. The cells were kept in continuous exponential growth by frequent reculturing every second or third day. During reculturing, as well as during experiments, the cells were kept in humidified $CO_2$ incubators at 37° C.

In the experiments represented in this example, the proteinaceous CANP inhibitor was additionally purified by gel filtration chromatography. The molecular weight and purity were assessed by polyacrylamide gel electrophoresis, the molecular weight being on the order of 57.500 Dalton.

Cell survival studies were performed by adding inhibitors to exponentially growing, asynchronous cells 2 hours after seeding the cells into plastic Petri dishes at known cell densities. The inhibitor treatment period was 24 hours after which the dishes were rinsed with warm (37° C.) Hanks' balanced salt solution and fresh medium without inhibitor, was added. After 12 to 14 days of incubation (with a medium shift on day 7) colonies of cells were fixed in ethanol and stained with methylene blue. Only colonies containing more than 40 cells were scored as survivors. The percent cell survival is calculated relative to untreated, control dishes.

The results represented in FIG. 1 show that calpain inhibitor I induced the greatest cytotoxic effect in cultures of human NHIK 3025 cervix carcinoma cells. Leupeptin and E-64 induced little cytotoxic effect. It appears that calpain inhibitor II induced slightly greater cytotoxicity than aprotinin.

Figure 2:
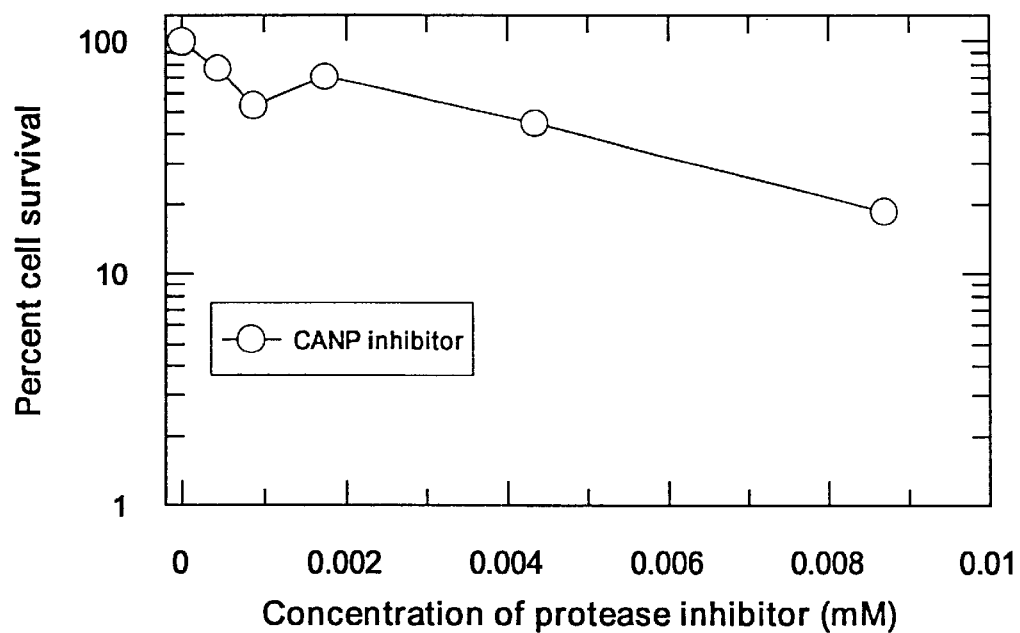
FIG. 2 is a graph showing the effect of CANP inhibitor on cell survival of human NHIK 3025 cervix carcinoma cells in vitro.

However, far greater cytotoxicity based upon molar concentrations was induced by chromatographically purified endogenous inhibitor of CANPs, as shown in FIG. 2.

EXAMPLE 6

The effect of calpain inhibitor I and calpain inhibitor II on growth of Walker rat tumors in vivo.

Figure 3:
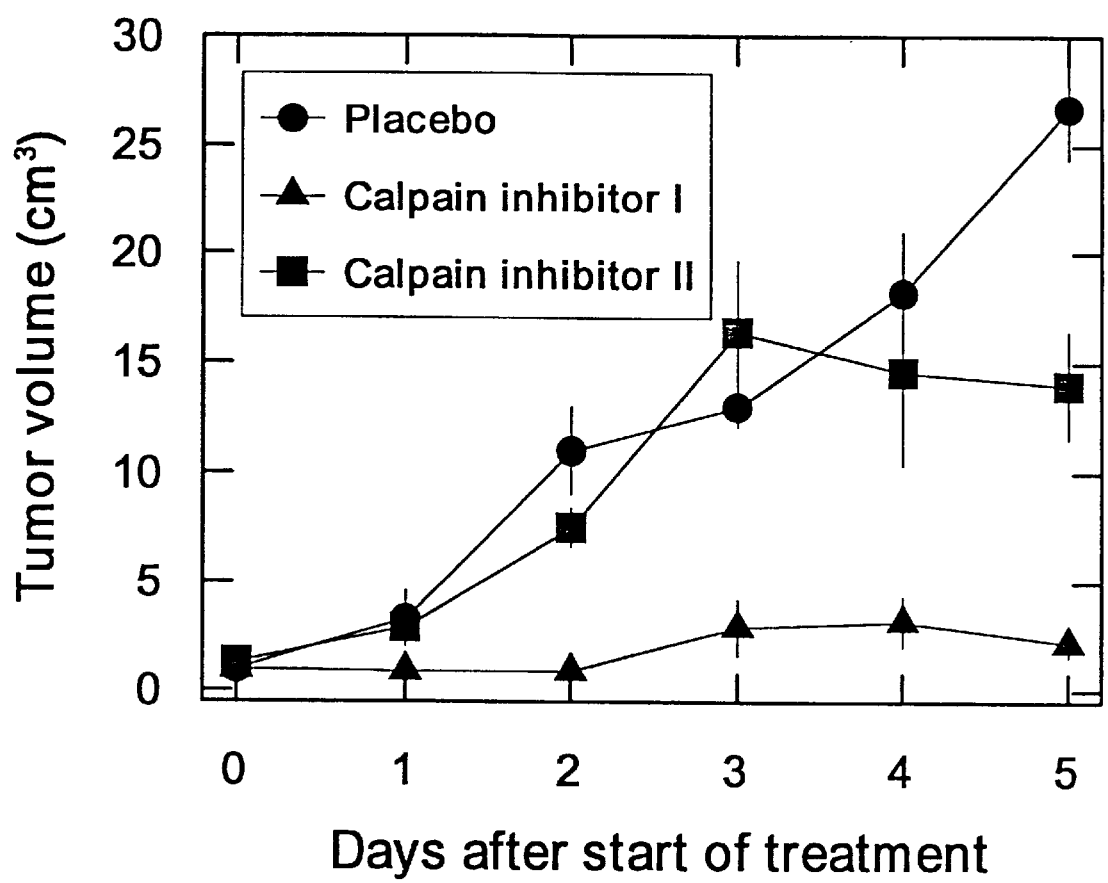
FIG. 3 is a graph showing the effect of calpain inhibitors I and II on growth of Walker rat tumors.

Male Wistar rats were injected with $10 \times 10^6$ Walker tumor cells per rat at the inguinal region. Treatment was started when measurable tumors appeared. Each treatment group consisted of 5 rats. Calpain inhibitor I and calpain inhibitor II were formulated into egg lecitin and phosphatyl choline-containing liposomes. Rats were treated with 2 ml liposomal solution of inhibitors at a concentration of 13.5 mg/ml, equivalent to 27 mg/100 g rat, daily by intraperitoneal injection. Rats in the control group received daily injections of saline-filled liposomes. Tumor volume was determined by measuring two diameters with calipers. The data is presented in FIG. 3 in which each data point represents the mean±S.E. tumor volume measurements for 5 rats.

The results show that 5 doses of calpain inhibitor I induced approximately 92% tumor regression. Calpain inhibitor II appears to induce an anticancer effect from the fourth dose.

Histological examination of the testis of the treated groups showed spermatogenetic arrest while the control group showed normal spermatogenesis. All other organs, including the liver, showed no cytotoxicity.

EXAMPLE 7

The use of CANP inhibitors against spermatogenesis (meiosis).

Four groups, each of five male Wistar rats, were used for testing CANP inhibitors. The first group received 0.25U CANP inhibitor (Sigma, P-0787) per gr body weight i.p. daily for six days. The second group received 0.27 mg Calpain inhibitor I (in liposomes), the third 0.27 mg Calpain inhibitor II (in liposomes) per gr body weight i.p. daily for six days and the fourth control group, injections of saline-filled liposomes. The following day after the last treatment, all rats were sacrificed and all organs including the testis were removed and examined histologically.

Histological examination of the testis of the rats treated with CANP inhibitors showed spermatogenetic arrest. The seminiferous tubules were devoid of spermatozoa and spermatids with degeneration of secondary spermatocytes and presence of degenerated spermatozoa in the lumen. The placebo rats showed testis with intact spermatozoa, spermatids and spermatocytes in all seminiferous tubules. All other organs of treated and placebo rats showed no histological toxic effects.

The results show that CANP inhibitors are cytotoxic to spermatocytes dividing by meiosis and to spermatids and spermatozoa (identical to NVs of malignant cells), cellular products of meiosis. Hence, CANP inhibitors are antimeiotic agents.

What is claimed is:

1. A method for the cytotoxic treatment of tumors selected from the group consisting of carcinomas, melanomas and hematological malignancies, which comprises administering to a human or warm blooded animal in need of such treatment an effective amount of a CANP (calcium-activated neutral protease) inhibitor specific for CANP, thus inhibiting growth of the tumors.

2. The method according to claim 1, comprising administering the effective amount of a CANP inhibitor intramuscularly, subcutaneously, intraperitoneally or intravenously.

3. The method according to claim 1, wherein the effective amount of the inhibitor is from 1 mg/kg body weight per day to 25 mg/kg body weight per day.

4. The method according to claim 1, wherein the inhibitor is a tetrameric protein having a molecular weight of approximately 240,000 Dalton based on elution from gel filtration, is heat stable at neutral pH, is destroyed on digestion with trypsin, and is dissociated into subunits of a molecular weight of approximately 60,000 Dalton or lower by 0.1–1 mM Ca$^{2+}$, based on SDS(sodium dodecyl sulfate)-polyacrylamide gel electrophoresis.

5. The method according to claim 1, wherein the inhibitor is calpastatin having a molecular weight of approximately 70,000 Dalton being from erythrocytes.

6. The method according to claim 1, wherein the inhibitor is calpastatin having a molecular weight of approximately 110,000 Dalton being from liver.

7. The method according to claim 4, wherein the inhibitor is an endogenous native inhibitor isolated from a biological source selected from the group consisting of erythrocytes, brain, cardiac muscle, lung, spleen, liver, skeletal muscle, kidney and testis.

8. The method according to claim 4, wherein the inhibitor is isolated from rabbit skeletal muscle.

9. The method according to claim 4, wherein the inhibitor is produced synthetically.

10. A method according to claim 1, wherein the inhibitor is N-acetyl-leu-leu-norleucinal.

11. A method according to claim 1, wherein the inhibitor is N-acetyl-leu-leu-methioninal.

12. The method according to claim 4, wherein the inhibitor is an antimeiotic agent, against malignant cells showing meiotic cell division.

13. The method according to claim 5, wherein the inhibitor is an antimeiotic agent, against malignant cells showing meiotic cell division.

14. The method according to claim 6, wherein the inhibitor is an antimeiotic agent, against malignant cells showing meiotic cell division.

15. The method according to claim 10, wherein the inhibitor is an antimeiotic agent, against malignant cells showing meiotic cell division.

16. The method according to claim 11, wherein the inhibitor is an antimeiotic agent, against malignant cells showing meiotic cell division.

17. A method according to claim 1, wherein the inhibitor is in the form of a solution, powder, injection, tablet, capsule, pellet or a fast or sustained release preparation.

18. A method according to claim 1, wherein the inhibitor is proteinaceous.

19. A method according to claim 1, wherein the inhibitor is administered to a human or warm blooded animal having malignant cells in an amount sufficient to kill said cells.

* * * * *